United States Patent [19]

Suchy

[11] 4,291,058
[45] Sep. 22, 1981

[54] NAPHTHALENECARBOXYLIC ACID ESTERS

[75] Inventor: Milos Suchy, Pfaffhausen, Switzerland

[73] Assignee: Hoffmann-La Roche Inc., Nutley, N.J.

[21] Appl. No.: 74,214

[22] Filed: Sep. 10, 1979

Related U.S. Application Data

[63] Continuation of Ser. No. 909,585, May 25, 1978, abandoned.

[30] Foreign Application Priority Data

Jun. 7, 1977 [CH] Switzerland .................. 6995/77

[51] Int. Cl.³ .............................................. A01N 37/10
[52] U.S. Cl. .............................. 424/308; 424/DIG. 8; 560/100
[58] Field of Search .................. 424/308, DIG. 8; 560/100

[56] References Cited

U.S. PATENT DOCUMENTS 4,009,197 2/1977 Fried et al. .................. 560/100

OTHER PUBLICATIONS

Buta, et al., C. A., vol. 82 (1975), p. 27094p (1972-1976 Formula Index; 6793F).
Buta et al.; Phytochemistry, 1974, 13(7), pp. 1033-1035 (Eng.).

Primary Examiner—Allen J. Robinson
Attorney, Agent, or Firm—Jon S. Saxe; George M. Gould; William M. Farley

[57] ABSTRACT

Naphthalenecarboxylic acid esters of the formula

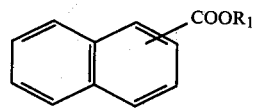

wherein $R_1$ is a lower alkynyl group, a process for their preparation, pesticidal compositions containing one or more of these compounds as the active ingredient and methods for using the pesticide compositions are disclosed.

3 Claims, No Drawings

NAPHTHALENECARBOXYLIC ACID ESTERS

This is a continuation of application Ser. No. 909,585 filed May 25, 1978, and now abandoned.

DETAILED DESCRIPTION OF THE INVENTION

This invention is directed to naphthalenecarboxylic acid ester of the formula

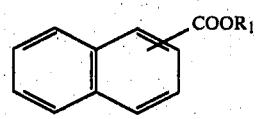

wherein $R_1$ is lower alkynyl and a process for its preparation.

This invention is also directed to compositions effective for pest control, and especially for insect control, which contain, as the active ingredient a naphthalenecarboxylic acid ester of formula I. Finally, the invention is directed to processes for the preparation of such compositions as well as methods for their use.

As used herein, the term "lower alkynyl" denotes both straight-chain and branched-chain monovalent, unsaturated aliphatic hydrocarbons of from 2 to 7 carbon atoms.

Preferred compounds of formula I are those wherein $R_1$ is an alkynyl of from 2 to 4 carbon atoms. Especially preferred are compounds wherein $R_1$ is the propargyl group, and, in particular, 2-propynyl 1-naphthoate.

The compounds of formula I include not only racemates but also optical isomers since one or two asymmetric carbon atoms can be present in the alcohol of formula III used to form the ester.

The compounds of formula I are prepared by reacting an acid of the formula

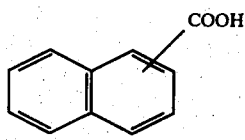

or a reactive derivative thereof, with an alcohol of the formula

wherein $R_1$ is lower alkynyl.

The reactive derivatives of the acid of formula II include acid halides, acid anhydrides, imidazolides, esters formed with a low boiling alcohol, alkali metal salts, silver salts and salts of a tertiary amine. Acid chlorides are the preferred acid halides.

Reactive derivatives of the alcohols of formula III include the halides and sulfonic acid esters.

The reaction is preferably carried out in an inert solvent either at room temperature or at temperatures above room temperature Preferred solvents include benzene, toluene and petroleum ether.

Reaction conditions are such as favor the removal of water as, for example, by carrying out the reaction in the presence of dicyclohexylcarbodiimide or by azeotropically distilling off the water formed in the reaction.

High yields of the compounds of formula I are obtained when the reactive derivative of the acid is an acid halide and the reaction with the alcohol is carried out at room temperature in the presence of a base. Acceptable bases are tertiary amines, e.g., pyridine or triethylamine, alkali metal hydroxides and alkaline earth metal hydroxides. Sodium hydroxide is a preferred base.

When the reactive derivative of the acid is an ester formed with a low boiling alcohol (e.g., methanol or ethanol) high yields of the naphthalenecarboxylic acid ester are obtained when the ester is heated with an alcohol of formula III in the presence of a base. A preferred base is an alkali metal alcoholate formed from the same low-boiling alcohol used in the formation of the reactive derivative of the acid of formula II.

The reaction of the ester reactive derivative of the acid of formula II by heating with the alcohol of formula III can also be carried out in the presence of sodium hydride in an inert solvent (e.g., toluene). The low-boiling alcohol formed during the reaction is removed by fractional distillation.

High yields of the compounds of formula I as also obtained by using, as the reactive derivative, the imidazolide of an acid of formula II. The imidazolide is reacted either with an alkali metal alcoholate derivative of an alcohol of formula III or with an alcohol of formula III in the presence of a catalytic amount of an alkali metal alcoholate. These reactions are preferably carried out at room temperature in an inert solvent such as tetrahydrofuran or dimethoxyethane.

When the reactive derivative of an acid of formula II is the acid anhydride, compounds of formula I are prepared by reacting the acid anhydride with an alcohol of formula III. The reaction is carried out at room temperature or, preferably, at an elevated temperature in the presence of an inert solvent such as toluene or xylene.

When a halide or a sulfonic acid ester of an alcohol of formula III is used as the reactive derivative, the acid of formula II is used as an alkali metal salt, a silver salt or a salt of a tertiary amine.

These salts are prepared in situ by adding the corresponding base to an acid of formula II. The reaction is carried out in a solvent, such as benzene, acetone or dimethylformamide, heated to or just below its boiling point.

The preferred acid halides of the alcohols of formula III are the acid chlorides and the acid bromides.

The ethyl esters of $\alpha$ and $\beta$-naphthalenecarboxylic acid are described in Ann. Chem. 422,196 and 422,200. The vinyl esters of $\alpha$- and $\beta$-naphthalenecarboxylic acid are described in Macromol. Chem. 18/19, 227 (1946).

The naphthalenecarboxylic acid esters of this invention are active as pesticides and, in particular, as insecticides. Thus, the term "pesticide" as used herein includes insecticides. They are especially active against flies, larvae, caterpillars, bettles and aphids. They are effective chiefly as direct insecticides and acaricides although some of them have systemic activity. The vapor phase ovicidal activity of the naphthalenecarboxylic acid esters of this invention is a preferred activity.

These compounds are also of value for the control of pests on animals. For example, 2-propynyl 1-naphthoate, used in a concentration of $1 \times 10^{-6}$ g/cm$^2$, is 100% active against Spodoptera littoralis in the larval stage.

The present invention is also concerned with a method for providing a locus subject to or subjected to attack by pests free from such attack. This method comprises applying to said locus an effective amount of a pesticidal composition containing, as the active ingredient, a compound of formula I. The locus can be, for example, plants, animals, soil, objects and surfaces.

This invention is also directed to pesticidal compositions comprising compatible carrier material and, as the active ingredient, one or more of the compounds of formula I. Examples of compatible carrier material include inert diluents, wetting agents and solvents.

Since the compounds of formula I are, in general, insoluble in water and in order to effect uniform distribution of the active ingredient of the pesticide compositions according to this invention, the active ingredient can be mixed with adjuvants, i.e., compatible carrier material, conventionally used for pesticidal application so that they may be formulated into ready-for-use compositions, e.g., as solutions, emulsions, emulsifiable concentrates, dispersions, dusts or wettable powders.

In addition to these adjuvants, the pesticidal compositions of this invention can contain other active pesticides, insecticides, bactericides and fungicides.

For example, the compounds of formula I can be dissolved in a water-immersible solvent such as a high-boiling hydrocarbon which contains dissolved emulsifiers so that, upon addition to water, the naphthalenecarboxylic acid ester solutions act as self-emulsifiable oils.

The compounds of formula I can also be mixed with a wetting agent with or without an inert diluent to form a wettable powder which is soluble or dispersible in water. The active ingredient can also be mixed with inert diluents to form a solid or powdery product.

Inert diluents with which the compounds of formula I can be admixed are solid inert materials including powdery or finely divided solid materials such as clays, sands, talc, mica, fertilizers and the like. The resulting compositions can thus, either be in the form of dusts or can be compositions having a larger particle size.

Wetting agents suitable for use in the pesticidal compositions of this invention can be anionic, non-ionic or cationic.

Examples of anionic wetting agents which can be used in these compositions include soaps; fatty sulfate esters such as dodecyl sodium sulfate and cetyl sodium sulfate; fatty-aromatic sulfonates such as alkylbenzene sulfonates, or butylnapthalene sulfonates; complex fatty sulfonates such as the amide condensation product of oleic acid and N-methyltaurine and the sodium sulfate of dioctyl succinate.

Examples of non-ionic wetting agents include, for example, condensation products of fatty acids, fatty alcohols or fat-substituted phenols with ethylene oxide, or fatty acid esters and ethers of sugars or polyvalent alcohols or products which are obtained from the latter by condensation with ethylene oxide and the products which are known as block copolymers of ethylene oxide and propylene oxide.

Examples of cationic wetting agents include cetyl-trimethylammonium bromide and the like.

The pesticidal compositions of this invention can also be used in the form of an aerosol. Such compositions can contain, in addition to the propellant gas, which is a polyhalogenated alkane such as dichlorodifluoromethane, a co-solvent and a wetting agent.

For the different uses of the naphthalenecarboxylic acid esters of this invention, the quantities of active ingredient used can vary. For example, in the treatment of plants for the control of pests thereon, the compounds are used to an extent of about 10–1000 g/ha. In the treatment of animals for the control of ectoparasites thereon, the animal is conveniently dipped in a solution containing 10–500 ppm of active ingredient or sprayed with such a solution.

The naphthalenecarboxylic acid esters of this invention are also useful as synergists for carbamates and other conventional insecticides such as, for example, organophosphorus acid esters, chlorinated hydrocarbons and pyrethroids. The compounds of this invention are especially preferred as synergists for such insecticides as 1-naphthylmethylcarbamate, 2,3-(isopropylidenedioxy)phenylmethyl[(trichloromethyl)thio]-carbamate, O,O-dimethyl-s-(N-methyl-carbamoylmethyl)-dithiophosphate, hexachlorocyclohexane (γ-isomer), 2,2-dimethyl-3-(2-methyl-propenyl)cyclopropanecarboxylic acid 2-allyl-4-hydroxy-3-methyl-2-cyclopenten-1-one ester and 2,2-dimethyl-3-dichlorovinyl-cyclopropane carboxylic acid m-phenoxybenzyl ester.

The following Examples illustrate the invention.

EXAMPLE 1

4 g of 2-naphthoic acid are heated with 10 ml. of thionyl chloride to 70° C. and maintained at that temperature for 30 minutes. The mixture is cooled to 50° C. and the resulting clear yellow solution is evaporated at 50° C. using a water-jet vacuum. 3 ml. of propargyl alcohol in 5 ml. of pyridine are then added to the residue. This mixture is heated to 70° C. and maintained at that temperature for 15 minutes. After evaporation of the solvent using a water-jet vacuum, the residue is recrystallized from methanol to yield 2-propynyl 2-naphthoate, m.p. 68°–70° C.

By analogous procedures:

2-propynyl 1-naphthoate, $n_D^{20} = 1.6123$, is prepared from 1-naphthoic acid and propargyl alcohol;

2-pentynyl 2-naphthoate, $n_D^{20} = 1.5945$, is prepared from 2-naphthoic acid and 2-pentynyl alcohol;

2-pentynyl 1-naphthoate, $n_D^{20} = 1.5923$, is prepared from 1-naphthoic acid and 2-pentynyl alcohol;

3-butynyl 2-naphthoate, m.p. 53°–54° C., is prepared from 2-naphthoic acid and 3-butynyl alcohol;

3-butynyl 1-naphthoate, $n_D^{20} = 1.5957$, is prepared from 1-naphthoic acid and 3-butynyl alcohol;

1-ethyl-2-propynyl 2-naphthoate, m.p. 69°–70° C., is prepared from 2-naphthoic acid and ethylethynyl carbinol;

1-ethyl-2-propynyl 1-naphthoate, $n_D^{20} = 1.5720$, is prepared from 1-naphthoic acid and ethylethynyl carbinol;

4-(5-methyl-1-pentynyl) 2-naphthoate, $n_D^{20} = 1.5510$, is prepared from 2-naphthoic acid and 5-methyl-1-hexyn-4-ol;

4-(5-methyl-1-pentynyl) 1-naphthoate, $n_D^{20} = 1.5610$, is prepared from 1-naphthoic acid and 5-methyl-1-hexyn-4-ol;

1,1-dimethyl-2-propynyl 2-naphthoate, m.p. 60°–61° C., is prepared from 2-naphthoic acid and 3-methyl-1-butyn-3-ol and 1,1-dimethyl-2-propynyl 1-naphthoate, $n_D^{20} = 1.5765$, is prepared from 1-naphthoic acid and 3-methyl-1-butyn-3-ol.

EXAMPLE 2

A suspension of 5.3 g of 1-butyn-3-ol and 5 g of 1-naphthoyl chloride is cooled to −10° C. and 3.1 ml. of 35% sodium hydroxide are slowly added dropwise. The mixture is warmed to room temperature and stirred until it is neutral. The mixture is poured into ice-water and then extracted with ether. The ether solution is washed with 10% sodium hydroxide and with water and dried. After the ether is distilled off, the residue is recrystallized from methanol to yield 1-methyl-2-propynyl 1-naphthoate, m.p. 66°–68° C.

By analogous procedure 1-methyl-2-propynyl-2-naphthoate is prepared from 1-butyn-3-ol and 2-naphthoyl chloride.

The following Examples demonstrate the efficacy of the naphthalenecarboxylic acid esters as pesticides.

EXAMPLE 3

This Examples illustrates the efficacy of naphthalenecarboxylic acid esters as topical ovicides.

Leaf roundels of potato plants carrying an egg deposit of ca 30 eggs of Leptinotarsa decemlineata were placed in small plastic dishes on a moist base. The eggs were treated topically with $10^{-3}$ ml. of an acetonic solution of an active ingredient (a.i.). The concentration of active ingredient in the solution was such as to apply $1 \times 10^{-x}$ grams of active ingredient on 1 cm² of egg deposit. The eggs were then incubated at 25° C. and 60% relative humidity until the larvae hatched. Freshly hatched larvae were fed with potato leaves and observed for 2 days. The results, expressed as percent reduction of the $F_1$-generation (larvae still alive after 2 days), for representative naphthalenecarboxylic acid esters are tabulated below in Table I.

TABLE 1

| Active Ingredient | Concentration a.i.,g/cm² of egg deposit | Percent Reduction, $F_1$-generation |
| --- | --- | --- |
| 2-Propynyl 2-naphthoate | $1 \times 10^{-5}$ | 100 |
| 2-Propynyl 1-naphthoate | $1 \times 10^{-5}$ | 100 |

EXAMPLE 4

This Example illustrates the vapor phase efficacy of naphthalenecarboxylic acid esters as ovicides.

The under surface of the lid of a Petri dish was sprayed with an aqueous spray liquor containing 2-propynyl 2-naphthoate so that the surface was coated with $10^{-x}$ g of active ingredient (a.i.) per cm². 15–30 eggs of the potato beetle (Leptinotarsa decemlineata) were placed in the body of the dish which was then covered with the treated lid.

The eggs did not come into contact with the coated surface. Seven days after treatment, the hatching rate of the eggs and the number of surviving or dead larvae were determined. The results are tabulated below in Table 2.

TABLE 2

| g a.i./cm² | Percent reduction of: | |
| --- | --- | --- |
| | hatching rate | surviving larvae |
| $1 \times 10^{-5.7}$ | 100 | 100 |
| $1 \times 10^{-6.2}$ | 100 | 100 |
| $1 \times 10^{-6.7}$ | 1 | 1 |

EXAMPLE 5

Following the experimental procedure described in Example 4, the efficacy of 2-propynyl 2-naphthoate against Epilachna chrysomeline (cucumber beetle) was evaluated. The results are tabulated below in Table 3.

TABLE 3

| g a.i./cm² | Percent reduction of: | |
| --- | --- | --- |
| | hatching rate | surviving larvae |
| $1 \times 10^{-5.7}$ | 100 | 100 |
| $1 \times 10^{-6.2}$ | 100 | 100 |
| $1 \times 10^{-6.7}$ | 4 | 4 |

EXAMPLE 6

Following the experimental procedure described in Example 4, the efficacy of 2-propynyl 2-naphthoate against Ostrinia nubilalis (corn bore) was evaluated. The results are tabulated below in Table 4.

TABLE 4

| g a.i./cm² | Percent reduction of the hatching rate |
| --- | --- |
| $1 \times 10^{31\ 5.7}$ | 100 |
| $1 \times 10^{-6.2}$ | 100 |
| $1 \times 10^{-6.7}$ | 0 |

EXAMPLE 7

This Example illustrates a typical pesticidal composition.

The following ingredients are admixed to prepare an emulsifiable concentrate.

| Ingredient | Amount |
| --- | --- |
| Active ingredient, a naphthalenecarboxylic acid ester of formula I | 500 g |
| Condensation product of an alkylphenol and ethylene oxide | 100 g |
| Epoxidated soya oil eith an oxirane oxygen content of ca 6% | 25 g |
| Butylated hydroxytoluene | 10 g |
| Xylene | to 1 liter |

EXAMPLE 8

The following ingredients are admixed to prepare an emulsifiable concentrate.

| Ingredient | Amount |
| --- | --- |
| Active ingredient, a compound of formula I | 500 g |
| Calcium dodecyl-benzenesulfonate | 100 g |
| Epoxidated soya oil with an oxirane oxygen content of ca. 6% | 25 g |
| Butylated hydroxytoluene | 25 g |
| Xylene | to 1 liter |

I claim:

1. A method for the control of insects and acarids which comprises topical application to the insects and acarids of an amount of an insecticidal and acaricidal composition comprising a compatible carrier material and a compound of the formula

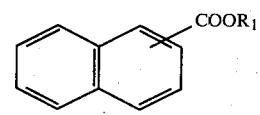

where $R_1$ is lower alkynyl which is effective as an insecticide and acaricid.

2. The method of claim 1 wherein the active ingredient in the insecticidal and acaricidal composition is 2-propynyl 2-naphthoate.

3. The method of claim 1 wherein the active ingredient in the insecticidal and acaricidal composition is 2-propynyl 1-naphthoate.

* * * * *